United States Patent [19]

Neithamer et al.

[11] Patent Number: 5,350,723
[45] Date of Patent: Sep. 27, 1994

[54] PROCESS FOR PREPARATION OF MONOCYCLOPENTADIENYL METAL COMPLEX COMPOUNDS AND METHOD OF USE

[75] Inventors: David R. Neithamer; James C. Stevens, both of Midland, Mich.

[73] Assignee: The Dow Chemical Company, Midland, Mich.

[21] Appl. No.: 884,966

[22] Filed: May 15, 1992

[51] Int. Cl.⁵ .............................................. C08F 4/64
[52] U.S. Cl. ........................... 502/104; 502/103; 502/117; 502/152; 502/155; 526/126; 526/170; 556/11; 556/52
[58] Field of Search ............... 502/103, 104, 117, 152, 502/155; 556/11, 52

[56] References Cited

U.S. PATENT DOCUMENTS

| | | |
|---|---|---|
| 4,400,301 | 8/1983 | Candlin et al. ............... 252/429 B |
| 4,897,455 | 1/1990 | Welborn, Jr. ...................... 526/129 |
| 5,026,798 | 6/1991 | Canich .............................. 526/127 |
| 5,064,802 | 11/1991 | Stevens et al. ................... 502/155 |
| 5,066,741 | 11/1991 | Campbell, Jr. .................... 526/160 |

FOREIGN PATENT DOCUMENTS 426637 8/1991 European Pat. Off. .

OTHER PUBLICATIONS

J. Am. Chem. Soc. 113, 8570–8571, (1991).
J. Orgmetallic Chem. 369, C13–C17 (1989).
J. Am. Chem. Soc. 100, 2389–2399 (1978).

*Primary Examiner*—Joseph L. Schofer
*Assistant Examiner*—David Wu

[57] ABSTRACT

Cationic Group 4 or Lanthanide metal catalysts containing a single, delocalized n-bonded group are prepared by contacting a metal complex with a carbonium salt of a compatible, non-coordinating anion.

5 Claims, No Drawings

PROCESS FOR PREPARATION OF MONOCYCLOPENTADIENYL METAL COMPLEX COMPOUNDS AND METHOD OF USE

BACKGROUND OF THE INVENTION

This invention relates to a method for preparing composition of matter that are useful as catalysts, and to a method of using these catalysts for polymerizing addition polymerizable monomers. More particularly the present invention relates to an improved method for preparing a class of catalysts known as constrained geometry catalysts.

In U.S. Ser. No. 545,403, filed Jul. 3, 1990, (published in equivalent form Mar. 13, 1991 as EP-A-516,815) there are disclosed certain constrained geometry metal complexes and catalysts derived by reacting the metal complex with activating cocatalyst. In U.S. Pat. No. 5,064,802 published Mar. 20, 1991 in equivalent form as EP-A-418,044) there are disclosed certain further constrained geometry metal catalyst formed by reacting such metal complexes with salts of Bronsted acids containing a non-coordinating compatible anion. The reference discloses the fact that such complexes are usefully employed as catalysts in addition polymerizations. In U.S. Ser. No. 720,041, filed Jun. 24, 1991, now abandoned, an alternative technique for preparing cationic constrained geometry catalysts by anion abstraction using borane compounds is disclosed. For the teachings contained therein, the foregoing United States patent and applications are herein incorporated by reference.

It has been previously known in the art to employ carbonium, oxonium or sulfonium ions to generate cationic bis-cyclopentadienyl Group 4 metal catalysts. Such a process is disclosed in EP-A2 426,637 published May, 8, 1991.

It would be desirable if there were provided an improved method that would allow the production of even more efficient catalysts as well as an improved addition polymerization process utilizing such catalysts.

SUMMARY OF THE INVENTION

As a result of investigations carried out by the present inventors there is now discovered a new and improved method for the preparation of catalysts and an improved method for polymerization of addition polymerizable monomers.

In accordance with the present invention there is provided a process for preparing a cationic complex having a limited charge separated structure corresponding to the formula:

$$LMX_mX'_nX''_p{}^+A^-,$$

wherein:

L is a single, delocalized n-bonded group that is bound to M, containing up to 50 nonhydrogen atoms;

M is a metal of Group 4 or the Lanthanide series of the Periodic Table of the Elements;

X is a divalent substituent of up to 50 non-hydrogen atoms that together with L forms a metallocycle with M that imparts a constrained geometry to the metal active site;

X' is a neutral Lewis base ligand having up to 20 non-hydrogen atoms;

m and n are independently zero or one;

X" each occurrence is a monovalent moiety selected from hydride, halo, alkyl, aryl, silyl, germyl, aryloxy, alkoxy, amide, siloxy, and combinations thereof (e.g., haloalkyl, haloaryl, halosilyl, alkaryl, aralkyl, silyalkyl, aryloxyaryl, alkyoxyalkyl, amidoalkyl, amidoaryl, etc.) having up to 20 non-hydrogen atoms;

p is an integer equal to M-m-2, where M is the valence of M; and

A$^-$ is noncoordinating, compatible anion, the steps of the process comprising contacting:

a) a derivative of a Group 4 or Lanthanide metal corresponding to the formula:

$$LMX_mX'_nX''_{p+1},$$

wherein

L, M, X, m, X', n, X", and p are as previously defined, with b) a salt corresponding to the formula: 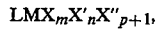©$^+$A$^-$, wherein ©$^+$ is a stable, carbonium ion containing up to 30 nonhydrogen atoms and A— is as previously defined; under conditions to cause abstraction of one X" and formation of the neutral species, ©X".

Such cationic complexes formed in the present invention are usefully employed in addition polymerization processes to prepare polymers, especially olefin polymers, for use in molding, film, sheet, extrusion foaming and other applications. Accordingly, a further embodiment of the present invention is a catalyzed addition polymerization process characterized in that the addition polymerization catalyst is a cationic complex formed according to the above process.

DETAILED DESCRIPTION

All references to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The term "carbonium ion" refers to cationic species that possess an electron deficient tri-coordinant carbon atom. Such ions are also referred to in the art as carbenium ions. Stable carbonium ions are such cationic species that are able to exist in solution without decomposition for a time period sufficient to undergo the reactions desired of the present invention. Preferred carbonium ions are those ions that are incapable of coordination with the metal atoms or metal complex. Examples include tropylium (cycloheptatrienylium), trityl (triphenylmethylium), benzene(diazonium) ions.

As used herein, the recitation "noncoordinating, compatible anion" means an anion which either does not coordinate to the metal containing portion of the complex or which is only weakly coordinated thereto thereby remaining sufficiently labile to be displaced by a neutral Lewis base. A noncoordinating, compatible anion specifically refers to a compatible anion which, within the time frame of the desired end use, when functioning as a charge balancing anion in the catalyst system of this invention does not transfer an anionic substituent or fragment thereof to said cation thereby forming a neutral four coordinate metal complex and a neutral metal byproduct. "Compatible anions" are also anions that are not degraded to neutrality when the initially formed complex decomposes and that are non-interfering with the desired subsequent polymerization or other uses of the complex.

More particularly the noncoordinating, compatible anion may comprise a single coordination complex comprising a charge-bearing metal or metalloid core, which anion is both bulky and non-nucleophilic. The recitation "metalloid", as used herein, includes nonmetals such as boron, phosphorus and the like which exhibit semi-metallic characteristics.

Preferably according to the present invention, there is provided a process for preparing a cationic complex having the foregoing, limiting, charge separated, structure wherein:

L is a single, delocalized n-bonded group that is bound to M, containing up to 50 nonhydrogen atoms:

M is a metal of Group 4 or the Lanthanide series of the Periodic Table of the Elements;

X is a divalent substituent of up to 50 non-hydrogen atoms that together with L forms a metallocycle where M that imparts a constrained geometry to the metal active site;

m is one;

X' is a neutral Lewis base ligand having up to 20 non-hydrogen atoms;

n is zero or one;

X'' each occurrence is a monovalent moiety selected from hydride, halo, alkyl, aryl, silyl, germyl, aryloxy, alkoxy, amide, siloxy, and combinations thereof (e.g. haloalkyl, haloaryl, halosilyl, alkaryl, aralkyl, silyalkyl, aryloxyaryl, alkyoxyalkyl, amidoalkyl, amidoaryl, etc.) having up to 20 non-hydrogen atoms;

p is an integer equal to M-3, where M is the valence of M; and

A⁻ is noncoordinating, compatible anion, the steps of the process comprising contacting:

a) a derivative of a Group 4 or Lanthanide metal corresponding to the formula:

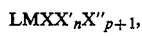

wherein

L, M, X, X', n, X'', and p are as previously defined; with b) a salt corresponding to the formula: ⓒ⁺A⁻, wherein ⓒ⁺ is a stable, carbonium ion containing up to 30 nonhydrogen atoms and A⁻ is as previously defined: under conditions to cause abstraction of one X'' and formation of the neutral species, ⓒX''.

By use of the term "constrained geometry" herein is meant that the metal atom is forced to greater exposure of the active metal site because one or more substituents on the substituted delocalized n-bonded group forms a portion of a ring structure including the metal atom, wherein the metal is both bonded to an adjacent covalently moiety and held is association with the substituted delocalized n-bonded group through an $\eta^5$ or other n-bonding interaction. It is understood that each respective bond between the metal atom and the constituent atoms of the substituted delocalized n-bonded group need not be equivalent. That is, the metal may be symmetrically or unsymmetrically n-bound to the substituted delocalized n-bonded group.

The geometry of the active metal site is further defined as follows. The center of the substituted delocalized n-bonded group may be defined as the average of the respective X, Y, and Z coordinates of the atomic centers forming the substituted delocalized n-bonded group. The angle, Θ, formed at the metal center between the center of the ligating atom of each other ligand of the metal complex may be easily calculated by standard techniques of single crystal X-ray diffraction. Each of these angles may increase or decrease depending on the molecular structure of the constrained geometry metal complex. Those complexes wherein one or more of the angles, Θ, is less than in a similar, comparative complex differing only in the fact that the constrain-inducing substituent is replaced by hydrogen have constrained geometry for purposes of the present invention. Preferably one or more of the above angles, Θ, decreases by at least 5 percent, more preferably 7.5 percent, compared to the comparative complex. Highly preferably, the average value of all bond angles, Θ, is also less than in the comparative complex.

Preferably, cationic complexes of Group 4 or Lanthanide metals prepared according to the present invention have constrained geometry such that the smallest angle, Θ, is less than 115°, more preferably less than 110°.

Substituted, delocalized n-bonded groups for use herein include any n-electrode containing moiety capable of forming a delocalized bond with the Group 4 or Lanthanide metal and further substituted with a divalent substituent that is also covalently bound to the metal. Divalent substituents preferably include groups containing up to 30 nonhydrogen atoms comprising at least one atom that is oxygen, sulfur, boron or a member of Group 14 of the Periodic Table of the Elements directly attached to the delocalized n-bonded group, and a different atom, selected from the group consisting of nitrogen, phosphorus, oxygen or sulfur that is covalently bonded to M. Examples of suitable delocalized, n-bonded groups are cyclopentadienyl- or alkyl-groups, and derivatives thereof.

By the term "derivative" when used to describe the above substituted, delocalized n-bonded groups is meant that each atom is the delocalized n-bonded group may independently be substituted with a radical selected from the group consisting of hydrocarbyl radicals, substituted-hydrocarbyl radicals wherein one or more hydrogen atoms are replaced by a halogen atom, hydrocarbyl-substituted metalloid radicals wherein the metalloid is selected from Group 14 of the Periodic Table of the Elements, and halogen radicals. Suitable hydrocarbyl and substituted-hydrocarbyl radicals used to form derivatives of the substituted, delocalized n-bonded group will contain from 1 to 20 carbon atoms and include straight and branched alkyl radicals, cyclic hydrocarbon radicals, alkyl-substituted cyclic hydrocarbon radicals, aromatic radicals and alkyl-substituted aromatic radicals. In addition two or more such radicals may together form a fused ring system or a hydrogenated fused ring system. Examples of the latter are indenyl-, tetrahydroindenyl-, fluorenyl-, and octahydrofluorenyl- groups. Suitable hydrocarbyl-substituted organometalloid radicals include mono-, di- and trisubstituted organometalloid radicals of Group 14 elements wherein each of the hydrocarbyl groups contains from 1 to 20 carbon atoms. More particularly, suitable hydrocarbyl-substituted organometalloid radicals include trimethylsilyl, triethylsilyl, ethyldimethylsilyl, methyldiethylsilyl, triphenylgermyl, trimethylgermyl and the like.

Substituted, delocalized n-bonded groups for use according to the present invention preferably are depicted by the formula:

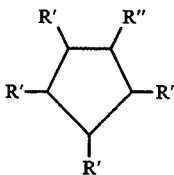

wherein:

R' each occurrence is hydrogen or a moiety selected from halogen, alkyl, aryl, haloalkyl, alkoxy, aryloxy, silyl groups, and combinations thereof of up to 20 non-hydrogen atoms, or two or more R' groups together form an aliphatic or aromatic fused ring system; and R" (which is a divalent X group) is a group that is covalently bonded to M of the formula: —Z—Y—, wherein Z is a divalent moiety comprising oxygen, boron, or a member of Group 14 of the Periodic Table of the Elements; and Y is a ligand group comprising nitrogen, phosphorus, oxygen or sulfur or optionally Z and Y together form a fused ring system; Y is a linking group covalently bonded to the metal comprising nitrogen, phosphorus, oxygen or sulfur, or optionally Z and Y together form a fused ring system.

In a highly preferred embodiment R" is:

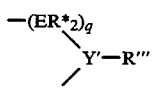

wherein:

E each occurrence is carbon, silicon, or germanium;

q is an integer from 1 to 4;

Y' is nitrogen or phosphorous; and

R* each occurrence is hydrogen or a moiety selected from alkyl, aryl, silyl, halogenated alkyl, halogenated aryl groups and combinations thereof having up to 20 non-hydrogen atoms, R" each occurrences is alkyl, aryl, silyl or a combination thereof (e.g. alkaryl, aralkyl, silyalkyl, etc.) having up to 10 carbon or silicon atoms; or two or more R* groups or one or more R* groups and R"' together form a fused ring system of up to 30 non-hydrogen atoms.

Highly preferred derivatives of a Group 4 or Lanthanide metal for use according to the invention correspond to the formula:

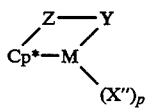

wherein:

M is zirconium or titanium;

Cp* is a cyclopentadienyl group; or a group selected from indenyl, fluoroenyl and hydrogenated derivatives thereof; or one of the foregoing groups substituted with one or more alkyl, aryl or cycloalkyl moieties of up to 20 carbons, said Cp* further being bound in an $\eta^5$ bonding mode to M and substituted by Z—Y;

Z is SiR*$_2$, CR*$_2$, SiR*$_2$SiR*$_2$, CR*$_2$CR*$_2$, CR*=CR*, CR*$_2$SiR*$_2$, or GeR*$_2$;

Y is a nitrogen or phosphorus containing group corresponding to the formula —N(R"")— or —P(R"")—; wherein:

R* each occurrence is hydrogen or a moiety selected from alkyl, aryl, silyl, halogenated alkyl, halogenated aryl groups and combinations thereof having up to 20 non-hydrogen atoms, and R"" is C$_{1-10}$ alkyl or C$_{6-10}$ aryl;

X" each occurrence is halo, alkyl, aryl, alkoxy, or aryloxy of up to 20 carbons; and p is 2.

Examples of the above most highly preferred metal coordination compounds include compounds wherein the R"" on the amido or phosphido group is methyl, ethyl, propyl, butyl, pentyl, hexyl, (including branched and cyclic isomers), norbornyl, benzyl, or phenyl; Cp* is cyclopentadienyl, tetramethylcyclopentadienyl, indenyl, tetrahydroindenyl, fluorenyl, tetrahydrofluorenyl, octahydrofluorenyl, or one of the foregoing groups further substituted with one or more methyl, ethyl, propyl, butyl, pentyl, hexyl, (including branched and cyclic isomers), norbornyl, benzyl, or phenyl groups; and X is methyl, neopentyl, trimethylosilyl, norbornyl, benzyl, methylbenzyl, phenyl, or pentafluorophenyl.

Illustrative derivatives of Group 4 or Lanthanide metals that may be employed in the practice of the present invention include: hydrocarbyl-substituted monocyclopentadienyl compounds such as:

cyclopentadienylzirconiumtrimethyl,
cyclopentadienylzirconiumtriethyl,
cyclopentadienylzirconiumtripropyl,
cyclopentadienylzirconiumtriphenyl,
cyclopentadienylzirconiumtribenzyl,
cyclopentadienyltitaniumtrimethyl,
cyclopentadienyltitaniumtriethyl,
cyclopentadienyltitaniumtripropyl,
cyclopentadienyltitaniumtriphenyl,
cyclopentadienyltitaniumtribenzyl,
cyclopentadienylhafniumdi(p-tolyl),
cyclopentadienyltitanium-2,4-pentadienyl,
pentamethylcyclopentadienylzirconiumtrimethyl,
pentamethylcyclopentadienylzirconiumtriethyl,
pentamethylcyclopentadienyl-zirconiumtripropyl,
pentamethylcyclopentadienyl zirconiumtriphenyl,
pentamethylcyclopentadienyl zirconiumtribenzyl,
pentamethylcyclopentadienyltitaniumtrimethyl,
indenylzirconium trimethyl,
indenylzirconium triethyl,
tetrahydroindenylzirconiumtripropyl,
indenylzirconiumtriphenyl,
indenylzirconiumtribenzyl,
indenyltitaniumtrimethyl,
indenyltitaniumtriethyl,
indenyltitaniumtripropyl,
indenyltitaniumtriphenyl,
tetrahydroindenyltitaniumtribenzyl,
indenylhafniumdi(p-tolyl),
cyclopentadienyltitaniumtriethyl,
pentamethylcyclopentadienyltitaniumtripropyl,
cyclopentadienyltitaniumtriphenyl,
pentamethylcyclopentadienyltitaniumtribenzyl,
pentamethylcyclopentadienylzirconiumtribenzyl,
pentamethylcyclopentadienyllanthanumdi(tris(-trimethyl silyl)methyl), etc.;

hydrocarbyloxy substituted compounds such as:

cyclopentadienyltitaniumtrimethoxide, cyclopentadienyltitaniumtriisopropoxide,
cyclopentadienyltitaniumtriphenoxide,
cyclopentadienyltitaniumtrimethoxide,
cyclopentadienyltitaniumtriisopropoxide,
cyclopentadienyltitaniumtriphenoxide,
pentamethylcyclopentadienyltitaniumtrimethoxide,
pentamethylcyclopentadienyltitaniumtriisopropoxide,
pentamethylcyclopentadienyltitaniumtriphenoxide,
pentamethylcyclopentadienylzirconiumtrimethoxide,
pentamethylcyclopentadienylzirconiumtriisopropoxide,
pentamethylcyclopentadienylzirconiumtriphenoxide,
indenyltitaniumtrimethoxide,
tetrahydroindenyltitaniumtriisopropoxide,
indenyltitaniumtriphenoxide,
tetrahydroindenylzirconiumtrimethoxide,
indenylzirconiumtriisopropoxide,
fluorenylzirconiumtriphenoxide,
octahydrofluorenylzirconiumtriphenoxide,
octahydrofluorenyltitaniumtribenzoxide, etc.;
halo substituted compounds such as:

cyclopentadienylzirconiumtrichloride,
cyclopentadienyltitaniumtrichloride,
indenyltitanium trichloride,
pentamethylcyclopentadienyltitaniumtrichloride,
pentamethylcyclopentadienylhafniumtrichloride,
cyclopentadienylosmium dichloride, etc.;
and compounds comprising mixtures of substituents such as cyclopentadienyltitaniumdimethylisopropoxide,
pentamethylcyclopentadienylzirconiummethyldichloride,
cyclopentadienyllanthanumchloroisopropoxide,
cyclopentadienyltitanium(tert-butylamino)methylchloride,
indenyltitanium(tert-butylamino)dibenzyl,
[(N-tert-butylamido)dimethyl($\eta^5$-cyclopentadienyl)silane]zirconiumdibenzyl,
[(N-tert-butylamido)dimethyl($\eta^5$-cyclopentadienyl)silane]zirconiumdimethyl,
[(N-tert-butylamido)dimethyl($\eta^5$-cyclopentadienyl)silane]titaniumdibenzyl,
[(N-tert-butylamido)dimethyl($\eta^5$-cyclopentadienyl)silane]titaniumdimethyl,
[(N-tert-butylamido)dimethyl(tetramethyl-$\eta^5$-cyclopentadienyl)silane]zirconiumdibenzyl,
[(N-tert-butylamido)dimethyl(tetramethyl-$\eta^5$-cyclopentadienyl)silane]zirconiumdimethyl,
[(N-tert-butylamido)dimethyl(tetramethyl-$\eta^5$-cyclopentadienyl)silane]titaniumdibenzyl,
[(N-tert-butylamido)dimethyl(tetramethyl-$\eta^5$-cyclopentadienyl)silane]titaniumdimethyl,
[(N-tert-butylamido)dimethyl($\eta^5$-indenyl)silane]zirconiumdibenzyl,
[(N-tert-butylamido)dimethyl($\eta^5$-tetrahydroindenyl)silane]zirconiumdimethyl,
[(N-phenylamido)dimethyl(tetramethyl-$\eta^5$-cyclopentadienyl)silane]titaniumdibenzyl,
[(N-tert-butylamido)dimethyl($\eta^5$-fluorenyl)silane]titaniumdimethyl,
[(tert-butylamido)tetramethyl-$\eta^5$-cyclopentadienyl)-1,2-ethanediyl]dimethylzirconium,
[(tert-butylamido)tetramethyl-$\eta^5$-cyclopentadienyl)-1,2-ethanediyl]titaniumdibenzyl,
[(N-methylamido)($\eta^5$-cyclopentadienyl)-1,2-ethanediyl]zirconiumdibenzhydryl,
[(N-methylamido)(tetramethyl-$\eta^5$-cyclopentadienyl)-1,2-ethanediyl]titaniumdineopentyl,
[(phenylphosphido)(tetramethyl-$\eta^5$-cyclopentadienyl)methylene]titaniumdiphenyl,
[(N-tert-butylamido)(di(trimethylsilyl))(tetramethyl-$\eta^5$-cyclopentadienyl)silane]zirconiumdibenzyl,
[(N-benzylamido)(dimethyl)($\eta^5$-cyclopentadienyl)silane]titaniumdi(trimethylsilyl),
[(phenylphosphido)dimethyl(tetramethyl-$\eta^5$-cyclopentadienyl)silane]zirconiumdibenzyl,
[(N-tert-butylamido)(dimethyl)(tetramethyl-$\eta^5$-cyclopentadienyl)silane]hafniumdibenzyl,
[(tetramethyl-$\eta^5$-cyclopentadienyl)-1,2-ethanediyl]titaniumdibenzyl,
[2-$\eta^5$-(tetramethylcyclopentadienyl)-1-methylethanolato-(2-)]titaniumdibenzyl,
[2-$\eta^5$-(tetramethylcyclopentadienyl)-1-methylethanolato-(2-)]titaniumdimethyl,
[2-$\eta^5$-(tetramethylcyclopentadienyl)-1-methylethanolato-(2-)]zirconiumdibenzyl,
[2-$\eta^5$-(tetramethylcyclopentadienyl)-1-methylethanolato-(2-)]zirconiumdimethyl,
[2-[(4a, 4b, 8a, 9, 9a,-$\eta$)-9H-fluoren-9-yl]cyclohexanolato(2-)]titaniumdimethyl,
[2-[(4a, 4b, 8a, 9, 9a,-$\eta$)-9H-fluoren-9-yl]cyclohexanolato(2-)]titaniumdibenzyl,
[2-[(4a, 4b, 8a, 9, 9a,-$\eta$)-9H-fluoren-9-yl]cyclohexanolato(2-)]zirconiumdimethyl,
[2-[(4a, 4b, 8a, 9, 9a,-$\eta$)-9H-fluoren-9-yl]cyclohexanolato(2-)]zirconiumdibenzyl, and the like.

Other compounds which are useful in the preparation of catalyst compositions according to this invention, especially compounds containing other Group 4 or Lanthanide metals, will, of course, be apparent to those skilled in the art.

In the most preferred embodiment —Z—Y— is an amidosilane or amidoalkane group of up to 10 nonhydrogen atoms, that is, (tert-butylamido)(dimethylsilyl), (tertbutylamido)-1-ethane-2-yl, etc.

Compounds useful as the second component in the preparation of the compounds of this invention will comprise a stable carbonium ion, and a compatible non-coordinating anion. Examples include tropillium tetrakispentafluorophenylborate, triphenylmethylium tetrakispentafluorophenylborate, benzene(diazonium) tetrakispentafluorophenylborate, tropillium phenyltrispentafluorophenylborate, triphenylmethylium phenyltrispentafluorophenylborate, benzene(diazonium) phenyltrispentafluorophenylborate, tropillium tetrakis(2,3,5,6-tetrafluorophenyl)borate, triphenylmethylium tetrakis(2,3,5,6-tetrafluorophenyl)borate, benzene(diazonium) tetrakis(2,3,5,6-tetrafluorophenyl)borate, tropillium tetrakis(3,4,5-trifluorophenyl)borate, triphenylmethylium tetrakis(3,4,5-trifluorophenyl)borate, benzene(diazonium) tetrakis(3,4,5-trifluorophenyl)borate, tropillium tetrakis(3,4,5-trifluorophenyl)aluminate, triphenylmethylium tetrakis(3,4,5-trifluorophenyl)aluminate, benzene(diazonium) tetrakis(3,4,5-trifluorophenyl)aluminate, tropillium tetrakis(1,2,2-trifluoroethenyl)borate, triphenylmethylium tetrakis(1,2,2-trifluoroethenyl)borate, benzene(diazonium) tetrakis(1,2,2-trifluoroethenyl)borate, tropillium tetrakis(2,3,4,5-tetrafluorophenyl)borate, triphenylmethylium tetrakis(2,3,4,5-tetrafluorophenyl)borate, benzene(diazonium) tetrakis(2,3,4,5-tetrafluorophenyl)borate, etc.

Preferred compatible noncoordinating anions are those containing a single coordination complex comprising a charge-bearing metal or metalloid core which anion is relatively large (bulky), capable of stabilizing the active catalyst species (the Group 3-10 or Lanthanide Series cation) which is formed when the two components are combined and said anion will be sufficient labile to be displaced by olefinic, diolefinic and acetylenically unsaturated substrates or other neutral Lewis bases such as ethers, nitriles and the like. Suitable metals include, but are not limited to, aluminum, gold, platinum and the like. Suitable metalloids include, but are not limited to, boron, phosphorous, silicon and the like. Compounds containing anions which comprise coordination complexes containing a single metal or metalloid atom are, of course, well known and many, particularly such compounds containing a single boron atom in the anion portion, are available commercially. In light of this, salts containing anions comprising a coordination complex containing a single boron atom are preferred.

Preferred compatible non-coordinating anions are tetrakis(pentafluorophenyl)borate, tetrakis (2,3,5,6-tetrafluorophenyl)borate, tetrakis(2,3,4,5-tetrafluorophenyl)borate, tetrakis(3,4,5-trifluorophenyl)borate, tetrakis(1,2,2-trifluoroethenyl)borate, and phenyltris(perfluorophenyl)borate.

In a most preferred embodiment of the present invention Cp*—Z—Y—M is (tert-butylamido)dimethyl(tetramethyl-$\eta^5$-cyclopentadienyl)silanetitanium, n is two, X is methyl or benzyl, and A⁻ is tetrakispentafluorophenyl borate.

With respect to the combination of first, metal containing component and carbonium salt to form a catalyst according to this invention, it should be noted that the two components must be selected so as to avoid transfer of a fragment of the anion, particularly an aryl group, or a fluorine or hydrogen atom to the metal cation, thereby forming a catalytically inactive species. This could be done by steric hindrance, resulting from substitutions on the cyclopentadienyl carbon atoms as well as substitutions on the aromatic carbon atoms of the anion. It follows that first components comprising perhydrocarbyl-substituted cyclopentadienyl radicals could be effectively used with a broader range of second compounds than could first components comprising unsubstituted cyclopentadienyl radicals. As the amount and size of the substitutions on the cyclopentadienyl radicals are reduced, however, more effective catalysts are obtained with second compounds containing anions which are more resistant to degradation, such as those with substituents on the ortho positions of the phenyl rings. Another means of rendering the anion more resistant to degradation is afforded by fluorine substitution, especially perfluoro-substitution, in the anion. Fluoro-substituted stabilizing anions may, then, be used with a broader range of first components.

The chemical reactions which occur in forming the catalysts of this invention may, when a preferred, boron containing compound is used as the second component, be represented by reference to the general formula set forth herein as follows:

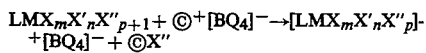

wherein L, M, X', X'', X, m, n, p and ©⁺ have the previously identified meanings, ©X'' is the neutral remnant of the carbonium ion, and Q is pentafluorophenyl.

In general, the stability of the neutral remnant of the carbonium ion causes the reaction to be driven to completion thereby resulting in increased yields of the desired cationic catalyst. Accordingly the resulting catalysts are extremely active and effective polymerization catalysts.

In general, the catalyst can be prepared by combining the two components in a suitable solvent at a temperature within the range from about −100° C. to about 300° C. The catalyst may be separately prepared prior to use by combining the respective components or prepared in situ by combination in the presence of the monomers to be polymerized. It is preferred to form the catalyst in situ due to the exceptionally high catalytic effectiveness of catalysts prepared in this manner. While the catalysts may not contain pyrophoric species, the catalysts' components are sensitive to both moisture and oxygen and should be handled and transferred in an inert atmosphere such as nitrogen, argon or helium.

The catalyst may be used to polymerize α-olefins and/or acetylenically unsaturated monomers having from 2 to about 18 carbon atoms and/or diolefins having from 4 to about 18 carbon atoms either alone or in combination. The catalyst may also be used to polymerize α-olefins, diolefins an/or acetylenically unsaturated monomers in combination with other unsaturated monomers. In a preferred embodiment the catalysts are employed to prepare copolymers of mixtures of vinyl aromatic monomers with olefins other than a vinyl aromatic monomer, specifically copolymers of styrene with ethylene or propylene. In general, the polymerization may be accomplished at conditions well known in the prior art.

Suitable solvents or diluents for the catalyst preparation and polymerization include any of the solvents known in the prior art to be useful as solvents in the polymerization of olefins, diolefins and acetylenically unsaturated monomers. Suitable solvents include, but are not necessarily limited to, straight and branched-chain hydrocarbons such as isobutane, butane, pentane, hexane, heptane, octane and the like; cyclic and alicyclic hydrocarbons such cyclohexane, cycloheptane, methylcyclohexane, methylcycloheptane and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexane, 3-methyl-1-pentene, 4-methyl-1-pentene, 1,4-hexadiene, 1-octene, 1-decene, styrene, and the like.

In a preferred embodiment, the catalyst is used to polymerize one or more $C_2$-$C_8$ α-olefins particularly ethylene or propylene, most preferably ethylene, at a temperature within the range from 0° C. to 300° C., preferably 25° C. to 200° C. and at a pressure within the range from atmospheric to 1000 psig (7 MPa) preferably 15 to 700 psig (0.1-4.9 MPa). In a most preferred embodiment of the present invention, the catalyst will be used either to homopolymerize ethylene or to copolymerize ethylene with a $C_3$-$C_8$ α-olefin (including styrene) thereby yielding a copolymer. In both the preferred and most preferred embodiments, the monomers will be maintained at polymerization conditions for a nominal holding time within the range from about 1 to about 60 minutes and the catalyst will be used at a concentration within the range from about $10^{-8}$ to about $10^{-1}$ moles per mole of monomer.

Having thus broadly described the present invention it is believed that the same will become even more apparent by reference to the following examples. It will be appreciated, however, that the examples are presented solely for the purpose of illustration and should not be construed as limiting the invention.

EXAMPLE 1

(Tert-butylamido)dimethyl(tetramethyl-$\eta^5$-cyclopentadienyl)silanetitaniumdimethyl and triphenylmethylium tetrakis-pentafluorophenyl borate (Tert-butylamido)dimethyl(tetramethyl-$\eta^5$-cyclopentadienyl)silanetitaniumdimethyl was prepared by reaction of methyllithium and the corresponding metal dichloride complex, which in turn was prepared by reaction of lithium 1,2,3,4-tetramethylcyclopentadienide with (N-t-butylamino)(dimethyl)silane chloride, followed by conversion to the dilithium salt, reaction with TiCl$_3$ to form the closed ring structure (N-t-butylamido)dimethyl(tetramethyl-$\eta^5$-cyclopentadienyl)titanium chloride, and oxidation of the metal center with methylene chloride to form (N-t-butylamido)dimethyl(tetramethyl-$\eta^5$-cyclopentadienyl)titanium dichloride.

A glass vial was charged with 41 mg of (tert-butylamido) (dimethyl)($\eta^5$-tetramethylcyclopentadienyl)silanetitanium dimethyl, 0.124 mmol) and 114 mg of triphenylmethylium tetrakis-pentafluorophenyl borate. Approximately 1 mL of $d^8$-toluene was added and the vial was shaken vigorously for about 5 minutes. A dark red-brown oil separated to the bottom of the vial leaving a pale orange solution above. Analysis of the pale orange solution by $^1$H and $^{13}$C NMR indicated the presence of 1,1,1-triphenylethane.

Polymerization 1

A 2 L Parr reactor was charged with 828 g of mixed hexanes solvent (Isopar™ E, available from Exxon Chemicals, Inc.) followed by 30 g of 1-octene. The reactor was heated to 150° C. and pressurized with ethylene to 500 psig (3.55 MPa). 25 $\Delta$psi (0.17 $\Delta$MPa) hydrogen chain control agent was then expanded into the reactor from a 75 ml hydrogen expansion tank. After several minutes, 2 mmole of (tert-butylamido)-dimethyl(tetramethyl-$\eta^5$-cyclopentadienyl)-silanetitanium dimethyl and 2 mmole of triphenylmethylium tetrakispentafluorophenyl borate (catalyst/cocatalyst) in toluene were pre-contacted and added to the reactor via a transfer line from a dry box. Upon addition of the metal complex/cocatalyst mixture to the reactor, a 25.5° C. exotherm was observed. After 9 min. the reaction was stopped and an antioxidant (Irganox™-1010, available from Ciba-Geigy, Inc.) was added to the polymer solution. The polymer was then dried to constant weight in a vacuum oven. 53.8 g. of an ethylene/octene copolymer having a melt index of 0.985 was obtained.

Polymerization 2

A 2 L Parr reactor was charged with 740 g of Isopar™ E followed by 118 g of 1-octene. The reactor was heated to 140° C. and pressurized with ethylene to 500 psig (3.55 MPa). 25 $\Delta$psi (0.17 $\Delta$MPa) hydrogen chain control agent was then expanded into the reactor. After several minutes, 2 mmole of (tert-butylamido)-dimethyl(tetramethyl-$\eta^5$-cyclopentadienyl)-silanetitanium dimethyl and 2 mmole of triphenylmethylium tetrakispentafluorophenyl borate (catalyst/cocatalyst) in toluene were pre-contacted and added to the reactor via a transfer line from a dry box. Upon addition of the catalyst/cocatalyst mixture to the reactor, a 5.5° C. exotherm was observed. After 15 min. The reaction was stopped and an antioxidant (Irganox-1010, available from Ciba-Geigy, Inc.) was added to the polymer solution. The polymer was then dried to constant weight in a vacuum oven. 24.0 g. of an ethylene/octene copolymer having a melt index of 0.626 was obtained.

EXAMPLE 2

The reaction conditions of Example 1 were substantially repeated using 0.5 $\mu$moles of the metal complex and 0.5 $\mu$moles of the carbonium salt each in 2 ml toluene solution to prepare the catalyst/cocatalyst in situ. The reaction temperature was 140° C. Upon addition of the cocatalyst to the reactor, a 17.9° C. exotherm was observed. After 15 min. the reaction was stopped and the polymer solution was charged to a receiver containing 100 mg Irganox 1010 and 10 ml isopropanol to kill the catalyst. The polymer was then dried to constant weight in a vacuum oven. Yield was 69.2 g. of an ethylene/octene copolymer having a melt index of 7.2.

EXAMPLE 3

The reaction conditions of Example 1 were substantially repeated. Accordingly, a 2 L Parr reactor was charged with 788 g of Isopar ™ E followed by 70 g of 1-octene. The reactor was heated to 120° C. and pressurized with ethylene to 500 psig (3.55 MPa). 38 $\Delta$psi (0.17 $\Delta$MPa) hydrogen chain control agent was then expanded into the reactor. After several minutes, 1 $\mu$mole of (tert-butylamido)dimethyl(tetrahydrofluorenyl)silanetitanium dimethyl (prepared in analogous manner to the metal complex of Example 1) in 2 ml toluene solution followed by 1 $\mu$mole of triphenylmethylium tetrakispentafluorophenyl borate in 2 ml toluene solution were added to the reactor. Upon addition of the cocatalyst to the reactor, a 34.9° C. exotherm was observed. After 15 min. the reaction was stopped and the polymer solution was charged to a receiver containing 100 mg Irganox 1010 and 10 ml isopropanol to kill the catalyst. The polymer was then dried to constant weight in a vacuum oven. Yield was 78.6 g. of an ethylene/octene copolymer having a melt index of 0.62.

What is claimed is:

1. A process for preparing a cationic complex comprising contacting:
   a) a derivative of a Group 4 or Lanthanide metal corresponding to the formula:

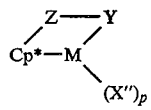

wherein:
   M is zirconium or titanium;
   Cp* is a cyclopentadienyl group; or a group selected from indenyl, fluorenyl and hydrogenated derivatives thereof; or one of the foregoing groups substituted with one or more alkyl, aryl or cycloalkyl moieties of up to 20 carbons, said Cp* further being bound in an $\eta^5$ bonding mode to M;

Z is $SiR^*_2$, $CR^*_2$, $SiR^*_2SiR^*_2CR^*_2CR^*_2$, $CR^*=CR^*$, $CR^*_2SiR^*_2$, or $GeR^*_2$;

Y is a nitrogen or phosphorus containing group corresponding to the formula —N(R'''')— or —P(R'''')—; wherein:

R* each occurrence is hydrogen or a moiety selected from alkyl, aryl, silyl, halogenated alkyl, halogenated aryl groups and combinations thereof having up to 20 non-hydrogen atoms, and R'''' is $C_{1-10}$ alkyl or $C_{6-10}$ aryl;

X' each occurrence is halo, alkyl, aryl, alkoxy, or aryloxy of up to 20 carbons; and p is 2, with b) a salt corresponding to the formula $©^+A^-$, wherein $©^+$ is a stable carbonium ion containing up to 30 nonhydrogen atoms and $A^-$ is a noncoordinating compatible anion;

under conditions to cause abstraction of one X'' and formation of the neutral species, $©X''$.

2. A process according to claim 1, wherein $©^+$ is triphenylmethylium or tropylium.

3. A process according to claim 1, wherein the metal complex and carbonium salt are combined in situ in an addition polymerization reaction.

4. A process according to claim 1 wherein X'' is methyl or benzyl.

5. A process according to claim 1 wherein $A^-$ is tetrakis(pentafluorophenyl)borate.

* * * * *

UNITED STATES PATENT AND TRADEMARK OFFICE
CERTIFICATE OF CORRECTION

PATENT NO. : 5,350,723

DATED : September 27, 1994

INVENTOR(S) : David R. Neithamer; James C. Stevens

It is certified that error appears in the above-identified patent and that said Letters Patent is hereby corrected as shown below:

Column 13, line 11, "X'" should correctly read --X"--.

Signed and Sealed this

Twentieth Day of June, 1995

*Attest:*

BRUCE LEHMAN

*Attesting Officer*  *Commissioner of Patents and Trademarks*